United States Patent
Rall

[11] Patent Number: 5,911,690
[45] Date of Patent: Jun. 15, 1999

[54] USE OF A PULSE OXYMETRY SENSOR DEVICE

[75] Inventor: Gerhard Rall, Bozzarisstrasse 39f, 81545 Munich, Germany

[73] Assignees: Reinhold Kintza, Kraiiling; Gerhard Rall, Munich, both of Germany

[21] Appl. No.: 08/849,285

[22] PCT Filed: Dec. 1, 1995

[86] PCT No.: PCT/EP95/04753

§ 371 Date: Sep. 10, 1997

§ 102(e) Date: Sep. 10, 1997

[87] PCT Pub. No.: WO96/16590

PCT Pub. Date: Jun. 6, 1996

[30] Foreign Application Priority Data

Dec. 1, 1994 [DE] Germany ............................. 44 42 855

[51] Int. Cl.$^6$ ....................................................... A61B 5/00
[52] U.S. Cl. ............................................ 600/313; 600/338
[58] Field of Search ..................................... 600/338, 313

[56] References Cited

U.S. PATENT DOCUMENTS

| | | | |
|---|---|---|---|
| 4,281,659 | 8/1981 | Farrar et al. | 128/635 |
| 4,299,232 | 11/1981 | Zilianti | 128/642 |
| 4,476,871 | 10/1984 | Hon | 128/642 |
| 4,658,825 | 4/1987 | Hochberg et al. | 128/634 |
| 4,798,588 | 1/1989 | Aillon | 604/122 |
| 4,825,879 | 5/1989 | Tan et al. | 128/633 |
| 4,913,151 | 4/1990 | Harui et al. | 128/634 |
| 4,936,306 | 6/1990 | Doty | 128/642 |
| 4,938,218 | 7/1990 | Goodman et al. | 128/633 |
| 4,944,307 | 7/1990 | Hon et al. | 128/748 |
| 5,050,613 | 9/1991 | Newman et al. | 128/670 |
| 5,099,842 | 3/1992 | Mannheimer et al. | 128/633 |
| 5,109,849 | 5/1992 | Goodman et al. | 128/633 |
| 5,139,033 | 8/1992 | Everett et al. | 128/785 |
| 5,154,175 | 10/1992 | Gunther | 128/633 |

(List continued on next page.)

FOREIGN PATENT DOCUMENTS

| | | |
|---|---|---|
| 2115715 | 8/1994 | Canada. |
| 0 097 454 | 1/1984 | European Pat. Off.. |
| 0 104 619 A2 | 4/1984 | European Pat. Off.. |
| 0 135 840 | 4/1985 | European Pat. Off.. |
| 0 442 011 | 8/1991 | European Pat. Off.. |
| 0 451 560 | 10/1991 | European Pat. Off.. |
| 0 522 674 A2 | 1/1993 | European Pat. Off.. |
| 0 586 025 A2 | 3/1994 | European Pat. Off.. |
| 2619471 | 11/1977 | Germany. |
| 2749048 | 5/1979 | Germany. |
| 3810008 | 10/1989 | Germany. |
| 43 04 693 A1 | 8/1994 | Germany. |
| 44 07 541 A1 | 10/1994 | Germany. |
| WO 89/09016 | 10/1989 | WIPO. |
| WO 90/01293 | 2/1990 | WIPO. |
| WO 90/04352 | 5/1990 | WIPO. |
| WO 93/18703 | 9/1993 | WIPO. |

OTHER PUBLICATIONS

"Noninvasie Pulse Oximetry Utilizing Skin Reflectance Photoplethysmography", IEEE Transactions on Biomedical Engineering, vol. 35, No. 10, pp. 798–805, Oct. 1988.

"König, Volker, FIG. 1–copy of slide shown in Kloster Banz, 8623 Staffelstein, Sep. 27–30, 1992".

*Primary Examiner*—Cary O'Connor
*Assistant Examiner*—Eric F. Winakur
*Attorney, Agent, or Firm*—Burns, Doane, Swecker & Mathis, L.L.P.

[57] ABSTRACT

The invention relates to the use of a pulse oximetry sensor device. Based on standard methods for recording material labor activity during birth, reliable signals may be created so that a midwife obtains measuring values indicating clear information of maternal labor activity. The invention suggests the use of a pulse oximetry sensor device which measures the change in the oxygen content in the fetal blood during birth. The pulse oximetry sensor device is provided with a least one light emitter and at least one receiver, connected with an analyzing device, and attached to the leading part of the fetus for recording the maternal labor activity.

9 Claims, 2 Drawing Sheets

U.S. PATENT DOCUMENTS

| | | | |
|---|---|---|---|
| 5,184,619 | 2/1993 | Austin | 128/639 |
| 5,188,108 | 2/1993 | Secker | 128/633 |
| 5,205,296 | 4/1993 | Dukes et al. | 128/775 |
| 5,217,013 | 6/1993 | Lewis et al. | 128/633 |
| 5,224,478 | 7/1993 | Sakai et al. | 128/633 |
| 5,246,003 | 9/1993 | DeLonzor | 128/633 |
| 5,247,932 | 9/1993 | Chung et al. | 128/633 |
| 5,279,308 | 1/1994 | DiSabito et al. | 128/775 |
| 5,373,852 | 12/1994 | Harrison et al. | 128/733 |
| 5,377,673 | 1/1995 | Van Dell et al. | 128/633 |
| 5,419,322 | 5/1995 | Joseph et al. | 128/634 |
| 5,421,329 | 6/1995 | Casciani et al. | 600/338 |
| 5,497,771 | 3/1996 | Rosenheimer | 128/633 |
| 5,551,424 | 9/1996 | Morrison et al. | 600/338 |
| 5,743,260 | 4/1998 | Chung et al. | 600/338 |

USE OF A PULSE OXYMETRY SENSOR DEVICE

BACKGROUND OF THE INVENTION

1. Field of the Invention

The invention relates to the use of a pulse oximetry sensor device during birth.

2. Description of the Related Art

A pulse oximetry sensor device for obstetric use is known for example, from DE 43 04 693. Such a sensor device is applied during birth on the leading part of the fetus. The sensor device includes a light emitter and a receiver. The light emitter sends a wavelength that radiates through the tissue of the fetus and is then picked up at least in part by the receiver. At the same time, the EKG of the fetus is measured. In order to be able to draw conclusions about the status of the fetus during birth, the signal occurring during a heart beat between diastole and systole is measured by the receiver. This measurement utilizes the absorption change caused by the arterial inflow of the blood as an indicator for the current fetal status.

During birth, a midwife needs additional information about the labor activity of the birthing mother. Data about the duration, starting time, peak, and end of a contraction are needed. If a midwife determines irregularities, this may be an indication of complications, so that the midwife must call in a physician who will induce further examination.

The use of intrauterine pressure catheters for measuring the labor activity is known. These pressure catheters are placed as a fixation device for standard pulse oximetry sensors between the uterus and fetus and are anchored there by an increase in volume. The catheter's balloon is used for measuring the intrauterine pressure by conducting the pressure to the outside via a tube and measuring the change in pressure at the tube connection. A disadvantage that may occur in the process is that the tube is clamped off during a contraction, so that differential signals can no longer be transmitted.

There is also a risk that germs are introduced into the uterus when inserting the catheter.

The present invention is based on the task of creating a process for recording the maternal labor activity that supplies reliable signals so that a midwife receives measuring values with clear meanings.

According to the present invention, this task is realized by using a pulse oximetry sensor device to measure the change in the oxygen content in the fetal blood during birth. The pulse oximetry sensor device is provided with at least one light emitter and one receiver, connector with an analyzing device, and attached on the leading part of the fetus for measuring the maternal labor activity.

The invention thus uses pulse oximetry in order to obtain information about the maternal labor activity. While in the past pulse oximetry has been used exclusively for monitoring the fetal status via pulse-synchronous pulse oximetry signals, experts were not able to recognize that pulse oximetry also can be used to obtain information about the status of the parturient.

If the pulse oximetry sensor device is attached, for example, to the scalp of the fetus located inside the opening of the cervical os, the blood volume in this part of the scalp rises during a contraction. The pressure between the cervical os and the fetal scalp is so high during a contraction that the venous backflow of the fetal blood is hindered, but is not sufficient to suppress the arterial inflow. The greater blood volume causes greater light absorption and a change in the sensor signal.

If the sensor device is located below the cervical os within the cervix, the opposite effect may occur. The fetal blood is pushed from the fetal tissue during a contraction, so that the light absorption measured by the sensor device decreases.

Thus, reliable signals about the maternal labor activity are always received. Good signals are even received if the fetus changes position during birth.

In a preferred method, the pulse oximetry sensor device can also be used to measure the fetal EKG. In this way, information about the fetal blood flow characteristics during contractions can be gained simultaneously. It is, for example, possible to display the fetal pulse-dependent or pulse-synchronous pulse oximetry signals in a first track, and the pulse oximetry signals for the mother's contractions in a second track.

According to another preferred method, the light emitter is able to output at least one wavelength at which the absorption of the oxygen-rich and oxygen-poor hemoglobin in the fetal blood is approximately equal. This essentially suppresses a signal change as a result of a change in the blood oxygen content. The point at which the absorption of the oxygen-rich hemoglobin (oxyhemoglobin) and oxygen-poor hemoglobin (deshemoglobin) are equal, is also called the isosbestic point.

In a variation of the invention, at least one wavelength emitted by the light emitter is approximately 805 nm. This wavelength is in the range of the isosbestic point. It makes it possible to obtain particularly clear and reliable signals.

In regard to the various types of hemoglobin with unique absorption spectra present in the blood, it is particularly beneficial if a wavelength is emitted at which the greatest possible number of hemoglobin types have the same absorption, or at which the absorption losses are as close together as possible.

BRIEF DESCRIPTION OF THE DRAWINGS

The invention will be described in greater detail with reference to the accompanying drawing wherein an exemplary embodiment of the present invention is illustrated, and wherein.

DESCRIPTION OF THE PREFERRED EMBODIMENT

Figure 1:
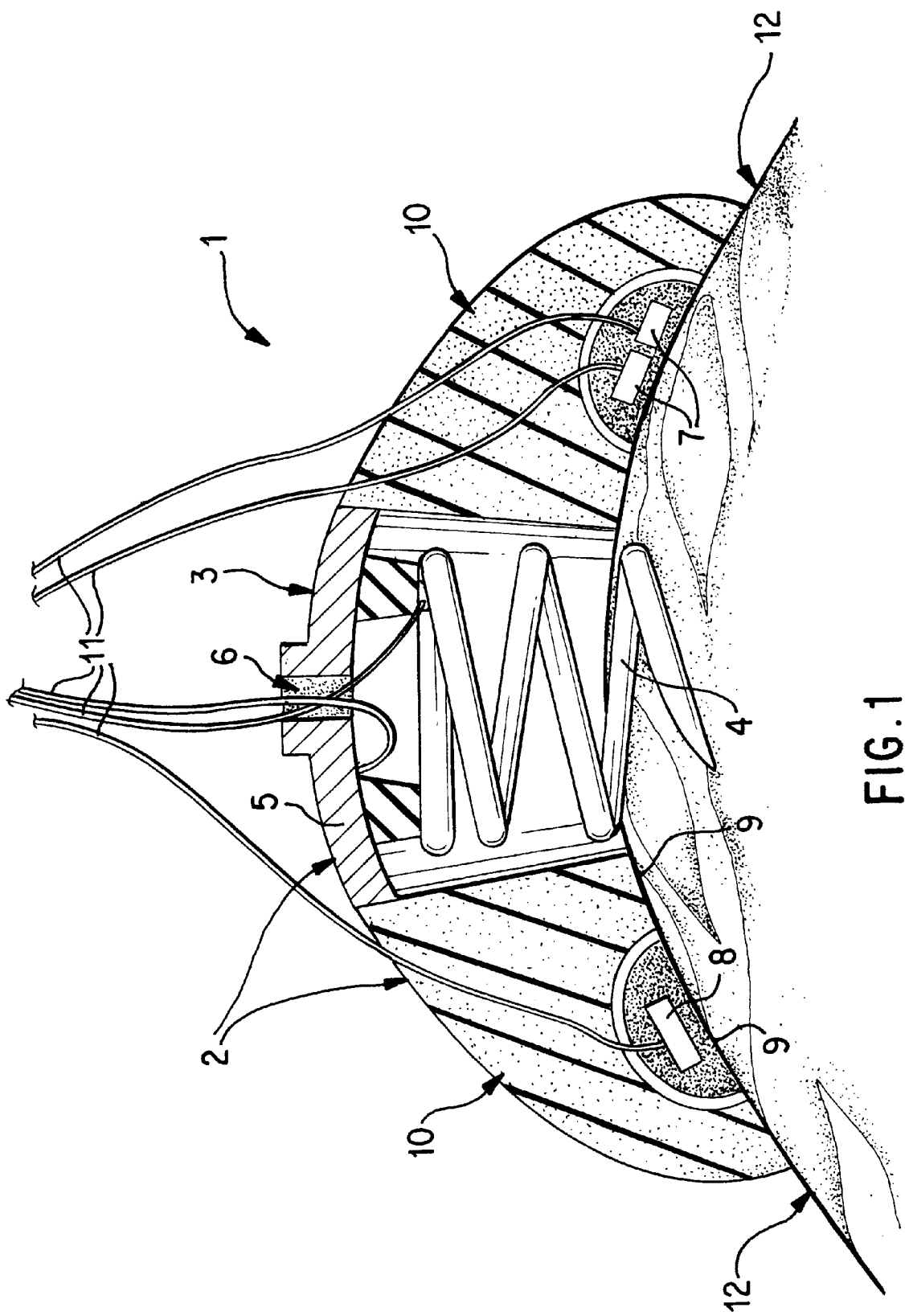
FIG. 1 shows a cross section through a pulse oximetry sensor device attached to the fetal scalp and suitable for use according to the invention.

FIG. 1 shows a pulse oximetry sensor device 1 as known from P 43 04 693, with an approximately round carrier 2. The carrier 2 has a centrically arranged attachment zone 3 with a wire spiral 4 and a metal plate 5. Metal plate 5 and wire spiral 4 are electrically insulated from each other. The metal plate 5 has a coupling part 6 located centrically on its top part.

The carrier 2 is provided around the attachment zone 3 with an elastic marginal zone 10, into which two light emitters 7 and a receiver 8 are imbedded. Light emitter 7 and receiver 8 adjoined the underside 9 of the sensor device 1 and are connected to electrical conductors 11 that exit from the top side of the sensor device 1.

In the same manner, the metal plate 5 and the wire spiral 4 are each connected to an electrical conductor 11 that exits from the top of the sensor device 1.

The wire spiral 4 projects from the underside 9 with approximately one winding turn. In FIG. 1, the wire spiral 4 is twisted with the lowest portion winding into the scalp 12 of a fetus. The carrier 2 hereby rests with a preload with its elastic marginal zone 10 on the fetal tissue 12.

Light emitter 7 and receiver 8 are located close to the scalp 12. The elasticity of the marginal zone 10 ensures that it is always in contact with the scalp 12 so that no light can penetrate from the outside between the light emitter 7, receiver 8, and the scalp 12.

Figure 2:
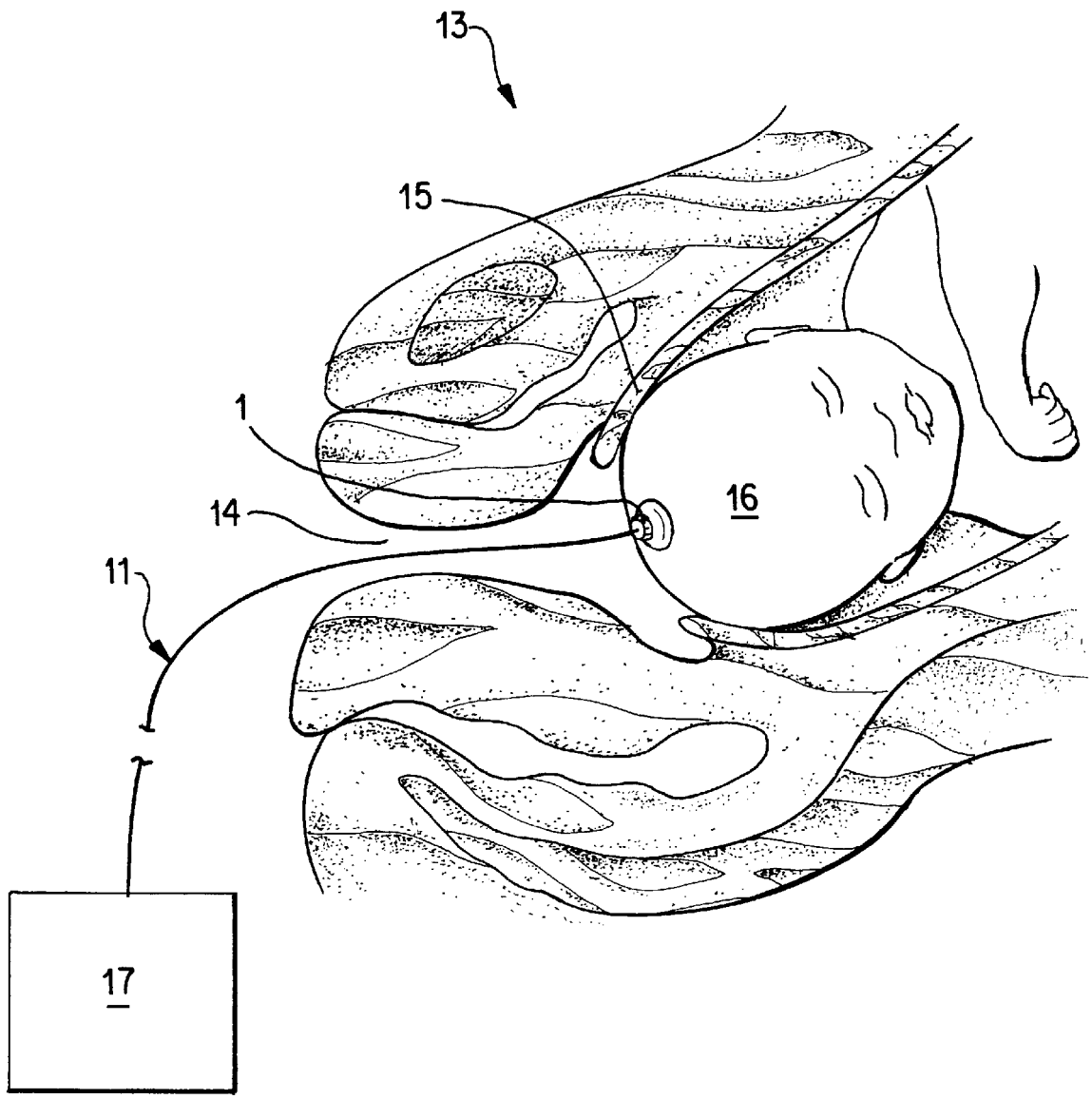
FIG. 2 shows a cross section of the abdomen of a parturient with a pulse oximetry sensor device attached to the fetal scalp.

FIG. 2 shows the abdomen 13 of a parturient in which the cervical os 14 is already open, and the amniotic sac 15 has burst. The fetal head 16 is partially visible through the cervical os 14.

The sensor device 1 from FIG. 1 is passed through the cervical os 14 and attached to the fetal scalp 12. An electrical conductor 11 connects the sensor device 1 with an analyzing device 17.

The use of the sensor device according to one embodiment of the present invention is explained in more detail below.

During birth, after the opening of the cervical os 14 and the bursting of the amniotic sac 15, the sensor device 1 is twisted with the wire spiral 4 into the scalp 12 of the fetus by means of a handling device that engages with the coupling part 6 of the sensor device 1. The wire spiral 4 is twisted inward until approximately one winding is twisted into the scalp 12, and the elastic marginal zone 10 rests with an elastic preload on the scalp 12. The electrical conductors 11 are passed to the outside through the cervical os 14 and are connected to an analyzing device 17.

When a contraction occurs, the blood stagnates in the area of the cervical os 14 because the venous backflow is prevented, but the arterial inflow is maintained at least in part. When the fetal tissue is irradiated by the light emitter 7, significantly more light is absorbed by the stagnating blood than in the absence of contractions. The signal obtained in the manner therefore differs from the signal obtain in the absence of contractions and appears as a peak on a recording strip of the analyzing device 17.

If the sensor 1 rests directly against the maternal tissue, the pressure of a contraction causes the blood to escape from this part of the fetal tissue. The absorption of the light through the blood is therefore smaller, so that a signal that differs from that in the absence of contractions is generated and is recorded by the recording medium of the analyzing device as a deviation.

The obtained signals are recorded along a time axis on a recording strip or are displayed on a monitor. Starting from an approximately straight line, each contraction appears like a wave crest. Based on the succession over time and the shape of the wave crests, the start, duration, peak and end of a contraction can be determined.

I claim:

1. A method of measuring maternal labor activity of a mother, the method comprising the steps of:

emitting light into a subject;

detecting a change in blood volume under a portion of a fetus's skin by measuring a change in an emission of said light through the blood under said portion; and using said detected change in blood volume to measure maternal labor activity of the mother.

2. The method according to claim 1, further comprising the step of detecting a contraction by evaluating the detected change in blood volume.

3. The method according to claim 1, wherein the portion is the scalp of the fetus.

4. The method according to claim 1, further comprising the steps of placing a light emitter on the portion of the fetus's skin, said light emitter emitting a predetermined wavelength of light.

5. The method according to claim 4, wherein the predetermined wavelength of light is measured with a light receiver.

6. The method according to claim 4, wherein the predetermined wavelength of light is substantially an isosbestic wavelength.

7. The method according to claim 1, further comprising the step of measuring the fetal EKG.

8. The method according to claim 1, wherein the change in blood volume is detected with a pulse oximetry sensor device.

9. The method according to claim 1, further comprising the step of recording the detected change in blood volume.

* * * * *